United States Patent [19]

Darnell

[11] 4,434,791
[45] Mar. 6, 1984

[54] SURGICAL RETRACTOR ARRAY SYSTEM

[75] Inventor: W. Dale Darnell, Caledonia, Miss.

[73] Assignee: Humboldt Products Corp., Columbus, Miss.

[21] Appl. No.: 358,082

[22] Filed: Mar. 15, 1982

[51] Int. Cl.³ .......................................... A61B 17/02
[52] U.S. Cl. ...................................... 128/20; 128/345
[58] Field of Search ................ 128/20, 341, 345; 24/130

[56] References Cited

U.S. PATENT DOCUMENTS

| | | | |
|---|---|---|---|
| 555,340 | 2/1896 | Schwarzmann | 24/130 |
| 2,586,488 | 2/1952 | Smith | 128/20 |
| 3,038,468 | 6/1962 | Raeuchle | 128/20 |
| 3,129,706 | 4/1964 | Reynolds | 128/20 |
| 3,515,129 | 6/1970 | Thuhan | 128/20 |
| 4,274,398 | 6/1981 | Scott | 128/20 |

FOREIGN PATENT DOCUMENTS 12990 of 1928 Australia ............... 128/20

Primary Examiner—Edward M. Coven
Assistant Examiner—Max F. Hindenburg
Attorney, Agent, or Firm—Beveridge, DeGrandi & Kline

[57] ABSTRACT

A surgical retractor system comprising an array of standardized, interchangeable, annular retractor frame sections of various shapes of which the end portions are configured to permit the interchangeable, hinged connection of the various shaped frames in forming generally annular retractor units adaptable to conform to fit the surface contours of various patients upon which a surgical operation is to be performed.

21 Claims, 9 Drawing Figures

U.S. Patent  Mar. 6, 1984  4,434,791
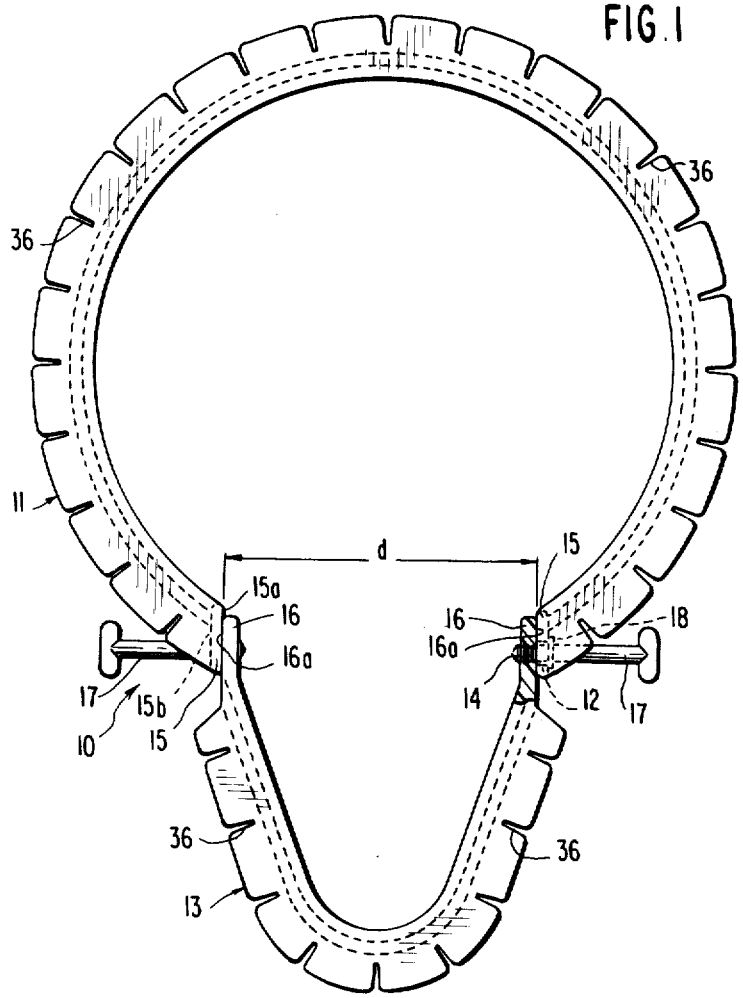
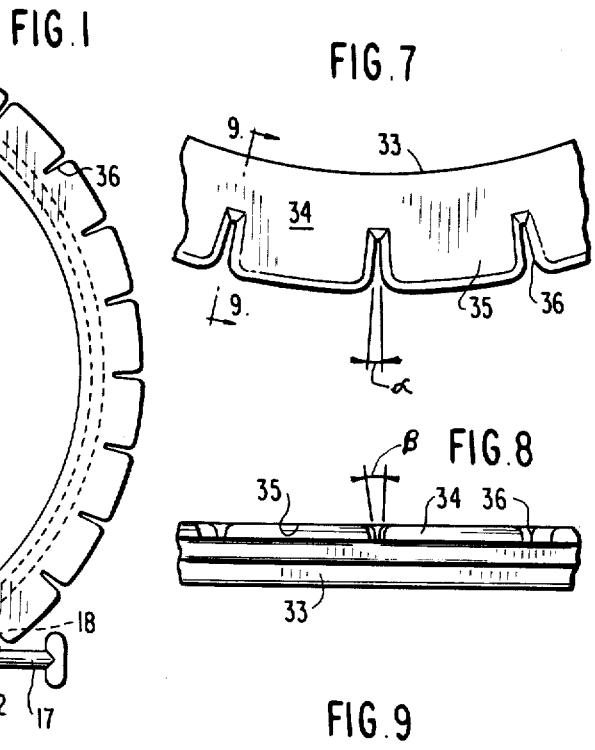
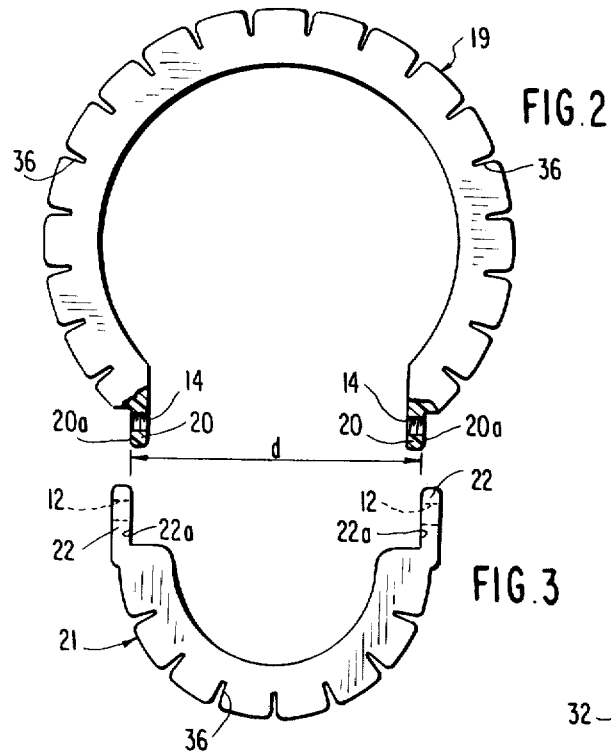
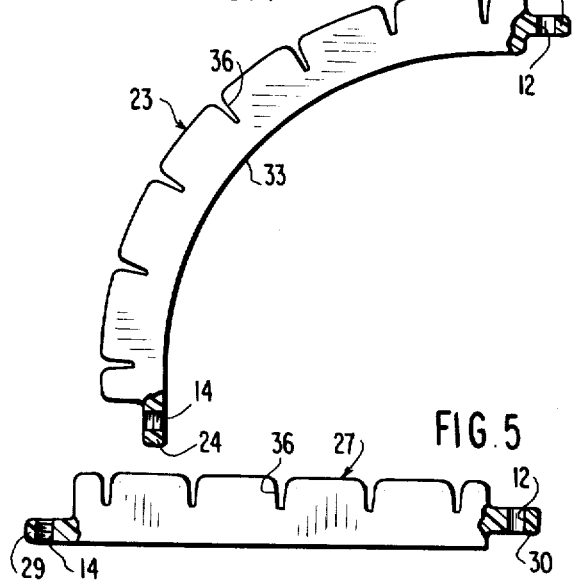

SURGICAL RETRACTOR ARRAY SYSTEM

BACKGROUND OF THE INVENTION

This invention relates to surgical apparatus and particularly to an array of universal surgical retractor frames comprising a system of retractor frames assemblable into a wide variety of surgical retractor units of different sizes and shapes adaptable for use on different portions of the bodies of surgical patients in performing a wide variety of operations.

U.S. Pat. No. 4,274,398 of Frank B. Scott, of which the assignee is the same as this invention and which patent is incorporated by reference in this specification, discloses a surgical retractor comprising an annular frame, which includes two sections hingedly connected, which are contoured to fit the surface of a surgical patient and around the exterior periphery of which are spaced apart notches into which both or one end portions of elastic tubing stay members are insertable and held by friction. The stay members of the Scott retractor extend across the interior of the retractor frame in contact with body tissue as a supporting or pinching member or have a tissue holding hook at one end which hooks into the tissue for retracting it and holding wounds open during the surgical operative process, as more fully described in the Scott patent. However, the surface body contours of different portions of the bodies of each surgical patient vary widely, and the same body portions of different patients vary considerably in size, e.g., an adult and a child, so that a wide variety of shapes and sizes of retractors is needed for surgical retractors of the general nature disclosed in the Scott patent. The hinged portions of a retractor must also be manipulated differently in some operations than in others. For example, in a mastectomy the two segments of a retractor must be rotatable relative to one another through 360° during the operation for raising the skin, which the Scott retractor of U.S. Pat. No. 4,274,398 will not allow. Further, different diameter elastic tubing is utilized as stay members for different purposes and patients, and the notches in the retractor must be contoured to frictionally hold the various sized tubes, e.g., adult stay member tubing conventionally has a 0.125 inch outside diameter and a 0.062 inch inside diameter, whereas pediatrics stay member tubing has a 0.085 inch outside diameter and a 0.040 inch inside diameter.

SUMMARY OF THE INVENTION

It is an object of the present invention to provide a simple system from which a wide variety of sizes and shapes of surgical retractors can be easily and quickly assembled in the operating room as the occasion arises for operating on different portions of bodies of both adult and child surgical patients.

It is another object of the invention to provide surgical retractor units of which the separate parts are rotatable relative to one another through 360° without restraint.

It is yet still another object of the present invention to provide surgical retractors which are capable of retaining all sizes of elastic stay tubing.

The foregoing and other objects of the invention have been achieved by providing an array of interchangeable retractor frame sections that are assemblable into generally annular, hinged surgical retractor units of a variety of sizes and shapes, that are conformable to a wide variety of body contours, of which the hinged parts of certain units can be rotated relative to one another without restraint, and in which the stay holding notches are contoured in two different planes such as will restrain the full range of sizes of stay member elastic tubing.

DESCRIPTION OF THE DRAWINGS

FIG. 1 is a plan view of the assembled, two ring type sections of an improved Scott type retractor of which the components comprise a portion of the retractor array system of my invention.

FIG. 2 is a plan view of another ring type frame section comprising a portion of the retractor array system of my invention.

FIG. 3 is a plan view of a further ring type frame section comprising a portion of the retractor array system of my invention.

FIG. 4, is a plan view of an arcuate type frame section comprising a portion of the retractor array system of my invention.

FIG. 5 is a plan view of a straight frame section comprising a portion of the retractor array system of my invention.

FIG. 6 is a plan view of an alternate straight frame section comprising a portion of the retractor array system of my invention.

FIG. 7 is an enlarged plan view of a typical portion of one of the curved retractor frame sections of FIGS. 1-4.

FIG. 8 is a front elevation view of FIG. 7.

FIG. 9 is a sectional view along section lines 9—9 of FIG. 7.

DESCRIPTION OF PREFERRED EMBODIMENTS

Referring first to FIG. 1, this illustrates an improved Scott type retractor 10, of which the improvements will be subsequently noted, comprising a relatively large horseshoe type ring frame 11, of which both end portions 15 contain unthreaded holes 12 in alignment in the plane of the frame, and a smaller lancet arch type frame 13 containing threaded holes 14 in alignment in the plane of the frame extending through each of the tab end portion extensions 16 that extend beyond the ends of the arch parallel to each other at the respective ends of the lancet arch frame 13 and are of a sufficient length to permit the lancet arch frame 13 to clear the horseshoe frame 11 when rotated relative to one another. The inwardly facing planar surfaces 15a of the end portions 15 of the horseshoe frame 11 are separated by the distance "d" which is also the dimension between the outwardly facing planar end surfaces 16a of the end tabs 16 of the lancet arch frame 13. The two retractor ring frames 11, 13 of the Scott retractor are hingedly connected by pins 17 having threaded ends with each pin passing through the unthreaded hole 12 in an end portion 15 of the horseshoe ring and threadedly engaging the threaded hole 14 in an end tab 16 of the lancet ring frame 13, the unthreaded holes 12 being larger in diameter than the threads of the pin 17 which has a collar 18 above the threaded portion that contacts the outwardly facing planar surface 15b extending beneath the end portion of the horseshoe ring 11 for tightening the two rings together. The outwardly facing end tab faces 16a of the lancet ring 13, that fit flush against the inwardly facing surface 15a of the horseshoe ring end portion 15, are also separated by the distance "d". Notches 36, which will be described subsequently in more detail, extend at spaced intervals around the outer periphery of both ring frames 11, 13 of the improved Scott retractor.

FIG. 2 illustrates another horseshoe arch type ring frame 19, about half again smaller in diameter than the Scott type horseshoe ring frame 11 with unthreaded end portions, but from each end of which extends parallel tab end portions 20 through each of which extends a threaded hole 14 of the same thread and diameter as the threaded holes 14 in the lancet ring 13 of the Scott retractor. The tab end portions 20 are of sufficient length to permit unrestricted rotation when mated with the Scott type horseshoe ring frame 11. The spacing between the outwardly facing surfaces 20a of the end tabs 20 of ring frame 19 is also "d", the same separation as the outwardly facing surfaces 16a of the end tabs 16 of the threaded lancet ring of the improved Scott retractor 10. Notches 36 extend around the outer periphery of the ring frame at spaced intervals.

FIG. 3 is an illustration of a round arch type ring 21 from the ends of which extend parallel tab end portions 22 pierced by unthreaded holes 12 of the same size as the unthreaded holes 12 in the ends of the unthreaded horseshoe ring 11 of the Scott retractor. The inwardly facing planar surfaces 22a of the tab end portions 22 are spaced-apart the same distance "d" as are the outwardly facing surfaces 20a of the end portions 20 of the threaded horseshoe frame 19 as well as the outwardly facing surfaces 16a of the threaded lancet arch ring 13. Notches 36 extend around the outer periphery of the ring at spaced intervals.

FIG. 4 illustrates an arcuate type frame section 23 which conveniently can be a 90° arc of a circle, although arcs of an ellipse or similar shape could also be utilized should the need arise. The configuration of arcuate frame 23 is substantially the same as a 90° segment of the unthreaded horseshoe frame 11 of the improved Scott retractor or the threaded horseshoe ring 19 of FIG. 2 with spaced-apart notches 36 on the outer periphery, but with each end configured in the form of extension tabs 24 and 25 that extend beyond the end of the frame at 90° to one another with one end tab 24 being pierced by a threaded hold 14 of the same thread and diameter as the threaded holes in the outer frames and the other tab 25 being pierced by an unthreaded hole 12 of the same size as the unthreaded holes 12 in the other frame sections of the array system. The end tab 25 containing the unthreaded hole 12 is offset from the inside rim perimeter 33 of the arcuate frame by the thickness of the threaded end tab 24 so that the threaded and unthreaded end tabs will nest and form a continuous frame section when two or more arcuate frame sections are joined together by a threaded pin 17.

Straight frame sections 27 and 28 are illustrated in FIGS. 5 and 6. Straight section 27 has tab end portions 29 and 30 extending from the ends with one end tab 29 having a threaded hole 14 of the same thread and diameter as the threaded holds in the other frame sections of the array and the other end tab 30 having an unthreaded hole 12 of the same configuration as the unthreaded holes of other frame sections. Notches 36 extend along one side of the frame at spaced intervals. The other straight frame section 28 is a reverse image of straight frame section 27 with a tab 31 containing a threaded hole 14 at one end and a tab end 32 containing an unthreaded hole 12 at the other end; the two frame sections 27 and 28 differing in being left and right hand sections with the notched sides facing outwardly when the threaded end tabs are on the same side. The unthreaded tabs 30 and 32 of the straight frames 27, 28 are offset from the unnotched side of the frame by the thickness of the threaded tabs 29 and 31, the threaded tabs 16, 20, 24, 29 and 31 of the various frames of the array having the same thickness so that the frame sections will fit together in a smoothly fitting contour when assembled, as will be subsequently described. Conveniently the tabs of the frames containing the unthreaded holes 12 can also be of the same thickness so that the collar 18 of the connecting pin 17 will contact the outer surfaces of the unthreaded portions of the ends of the frames and hold the frame sections together when joined together by threaded pins 17 in the same general manner as illustrated in the improved Scott retractor of FIG. 1. Straight frames 27, 28 can be of different lengths, for example four inches, five inches, six inches or any other length that would be required.

The cross-sectional configuration of the basic frame structure of the various frames of the array system of my invention, of which FIGS. 1-6 are typical, are the same, as is illustrated in FIGS. 7, 8 and 9. This configuration conforms in some respects to the frame configuration of the Scott retractor described in U.S. Pat. No. 4,274,398 but incorporates improved features to be subsequently described. As in the Scott retractor, each frame is formed of a rigid material, preferably a molded plastic. FIG. 9 illustrates the cross-section of a typical frame which has a relatively deep inner rim 33, the lower edge 33a of which rests on the body surface of the patient, with a thinner flange 34 having a flat surface 35 extending outwardly from the upper portion of the rim to the outer perimeter of the frame in a manner to leave a space beneath the outer portion of the frame and the patient for access by the surgeon when attaching and arranging the stays in the specially contoured notches 36 that extend into the frame upper flange 34 from the outside periphery at convenient spaced intervals along the length of the flange.

All frames of my invention are planar and are not individually contoured to fit the surface contours of the body to be operated on as is indicated for the frames in the Scott U.S. Pat. No. 4,274,398. By joining together the planar sections of the different frame shapes of the array of my invention, the hinged retractor will accommodate the various body contours of different patients. An adhesive, of which a two sided adhesive tape Specification T made by Three M is typical, is applied to the bottom surface 33a of the inner rim section 33 of each frame to adhere the frame to the patient's body and hold the frame in place.

Most importantly, all notches 36 in the retractor frames of my invention are contoured somewhat differently than the notches of the Scott retractor which are uniform in width along a major portion of their length as well as uniform in depth. The notches of my invention are wedge shaped both in the plane of the frame, as illustrated by the angle $\alpha$ in FIG. 7, and in a vertical plane perpendicular to that of the frame, as indicated by the angle $\beta$ in FIG. 8. The width variance of the notches along the notch length and the width variance of the notches along the notch depth are such as will accommodate and frictionally hold the various sizes of elastic tubing that are used in surgical operations, presently the adult stay tubing having an outside diameter of 0.125 inches and the pediatrics stay tubing having an outside diameter of 0.0085 inches.

All threaded hole tab end portion extensions 16, 20, 24, 29 and 31 of the variously shaped frame sections are sufficiently long that when affixed to the large horseshoe ring frame with unthreaded holes of the Scott retractor or other frames of the array having unthreaded holes in the end portions, the frames may be rotated through 360° without interference for operations requiring this, as in a mastectomy.

By connecting selected ones of the above-described frames having unthreaded hole end portions to frames with threaded hole end portions by means of threaded connecting pins 17, a wide variety of differently configured retractor units can be quickly and easily assembled from standardized frame sections for performing surgical operations on various body portions of different patients as the need arises. The combination of the unthreaded hole horseshoe 11 and the threaded hole lancet arch ring 13 of FIG. 1, with the improvements described herein to include the longer end tab 16, is not only most useful in performing operations described in the Scott U.S. Pat. No. 4,274,398 but can be used in performing mastectomies as previously discussed. A combination of the smaller horseshoe ring frame 19 with the threaded ends of FIG. 2 with the round arch ring 21 with unthreaded ends of FIG. 3, or a combination of the lancet arch frame 13 with threaded ends of FIG. 1 with the round arch ring 21 with threaded ends of FIG. 3, provides a retractor for pediatric operations, operations on delicate tissues, operations on small portions of the body such as the hands or feet, etc. A combination of the threaded end horseshoe ring 19 of FIG. 2 with the unthreaded end horseshoe ring 11 of FIG. 1 is used in O.B. operations. A flank retractor is produced by combining four arcuate frames 23 of FIG. 4 with four straight frames of FIG. 5, each straight frame being interposed between a pair of arcuate frames, or a smaller version could be made by combining the four arcuate frame members 23 of FIG. 5. A pair or more of straight frames, comprising left and right hand frames 27 and 28 of FIGS. 5 and 6, may be inserted between any two of the threaded hole ring frames and unthreaded hole ring frames of FIG. 1, 2 or 3 or between a pair of joined arcuate frames 23 of FIG. 4 to accommodate body contours requiring an elongated retractor.

It will be observed that the above described retractor system array of a relatively small number of variously shaped, planer retractor frames having threaded hole end portions fitting against the interior end portions containing unthreaded holes of other variously shaped frames provides a relatively large number of sizes and shapes of annular retractor units. Thus by stocking an array of interchangeable and standardized shapes of frames, retractors required for a wide variety of operations on various patients, old and young, can be economically and quickly provided as the need arises in the operating room.

Further combinations of the above described frames will become apparent as the need arises and it is contemplated that frame shapes of different annular configuration and dimensions than described which can be assembled with the frame embodiments described herein will be added to the array. However, all frame configurations need be sufficiently standardized that when assembled a generally annular unit is formed that is conformable to the body area immediately surrounding the area on which the operation is being performed. Further, although the means by which the various frame members are hingedly connected in the described embodiments is by means of threaded pins engaging threaded holes in frame members, it is contemplated that the end portions of the frame members could be adapted to be hingedly connected by other obvious mechanical means. It should be understood that the foregoing disclosure relates only to presently preferred embodiments of the invention and that numerous modifications or alterations of the basic concept of an array of universal retractor frame members of various shapes assemblable into annular, hinged surgical retractor units of a variety of configurations may be made without departing from the spirit and scope of the invention as set forth in the appended claims.

What is claimed is:

1. A universal, surgical retractor frame array system assemblable into a plurality of annular, hinged retractor frame units of various different annular shapes adaptable to conform to the surface contours of different body portions of surgical patients for retaining elastic tubing stay members inserted into notches spaced apart around each retractor frame unit periphery, said system comprising a plurality of rigid, planar frame sections of various outline shapes in the plane of the frame section, each frame section having a first straight end portion with a hole therethrough and a second straight end portion with a threaded hole therethrough, each frame section having a uniform transverse cross-section with contoured notches spaced apart and extending inwardly from a common side forming each retractor unit outer periphery when hingedly joined to other frame sections of said array system; and threaded connecting means for insertion through said end portion holes to releasably and hingedly connect the two end portions of each said frame section to the end portions of other frame sections of said array system to permit said frame sections to be releasably connected together to alternatively form any of various differently shaped, annular retractor frame units.

2. The retractor frame system of claim 1 wherein said plurality of frame sections includes a plurality of planar, major frame sections comprising open rings each defining the major portion of annuli of different radii and a plurality of planar, minor frame sections comprising arches of different shapes of which the end portions are adapted for fitting in flush alignment with the end portions of said major frame sections and hinged connection thereto.

3. The retractor frame system of claim 2 wherein the outer surfaces of the end portions of a minor frame section are dimensioned to fit flush against the interior surfaces of the end portions of a major frame section and the minor frame end portions comprise parallel straight segments of sufficient length to allow 360° relative rotation of said major and minor frame sections.

4. The retractor system of claim 2 wherein said plurality of frame sections further includes a plurality of straight planar frame sections having end portions adapted to be inserted between the respective end portions of said major and minor frame sections for hinged connection thereto.

5. The retractor frame system of claim 4 wherein said plurality of straight frame sections include at least one pair of straight frame sections, with one section of said pair being the reverse image of the other straight frame section of said pair.

6. The retractor frame system of claim 2 wherein both end portions of one of said major and minor frame sections comprises a first type of end portion adapted to fit flush against and outside both end portions of the other one of said major and minor frame sections and both end portions of the other one of said major and minor frame sections comprise a second type of end portion, one of said first and second types of end portion having the threaded hole therethrough.

7. The retractor frame section of claim 6 wherein said connecting means comprises a pin threaded at one end and said second type end portions contain the threaded hole to receive the threaded end of said pin.

8. The retractor frame system of claim 7 in which said pin includes a collar adjacent the threaded pin end for contacting one surface of said second type end portion and cooperating with the threaded pin end and the threaded hole to hold two frame sections together.

9. The retractor frame system of claim 1 wherein said plurality of frame sections includes a plurality of straight planar frame sections.

10. The retractor frame system of claim 9 wherein the first and second end portions of each frame sections are differently contoured such that one end portion of one frame section fits in overlapping alignment over an end portion of another frame section for forming a retractor unit having a smoothly contoured outline shape.

11. The retractor frame system of claim 9 wherein each said straight frame section has a first and a second type end portion with said first type end portion of each straight frame section adapted to fit flush over and outside the second type end portion of another frame section in the direction of the notched side when a plurality of frame sections are assembled into a retractor unit.

12. The retractor frame system of claim 1 wherein said plurality of frame sections includes a plurality of arcuate planar frame sections each comprising a ninety degree are from the ends of which protrude straight end portions adapted for hinged connection to other frame sections of said retractor system.

13. The retractor frame system of claim 12 wherein each said arcuate frame section has a first and a second type end portion with said first type end portion of each arcuate frame section adapted to fit flush over and outside the second type end portion of another frame section in the direction of the notched sides when a plurality of frame sections are assembled into a retractor unit.

14. The retractor frame system of claim 1 wherein said plurality of frame sections includes frame sections having first and second type end portions, with said first type end portions adapted to fit flush against and outside said second type end portions in the direction of the notched side when respective frame sections are assembled into a retractor unit.

15. The retractor frame system of claim 1 wherein said connecting means comprises a pin threaded at one end, and wherein said frame sections have first and second types of end portions with said first type end portions adapted to fit flush against and outside said second type end portions when respective frame sections are assembled into a retractor unit, said first type end portions having the unthreaded hole therethrough which said pin is insertable, and said second type end portions having the threaded hole therethrough adapted to receive the threaded end of said pin.

16. The retractor frame system of claim 15 in which said pin includes a collar adjacent the threaded pin end for contacting a surface of one of said frame section end portions and cooperating with the threaded pin end and the threaded hole to hold two frame sections together.

17. The retractor frame system of claim 1 wherein said plurality of frame sections includes arcuate planar frame sections each comprising a ninety degree arc from the ends of which extend straight end portions, and straight planar frame sections from the ends of which extend straight end portions, each said arcuate frame section having a first and a second type end portion and each said straight frame section having a first and a second type end portion, said first type end portions adapted to fit flush over and outside the second type end portions of an adjacent frame section when said arcuate and straight frame sections are assembled to form a retractor unit.

18. The surgical retractor frame system of claim 1 wherein said frame sections have an upper surface adapted to face away from the body of the surgical patient and a lower surface adapted to immediately overlie the body of the patient and wherein each of said notches has a contour tapered along a length dimension extending transversely of the frame section to diminish along said entire length dimension from a greater width dimension at the outer edge of the frame section to a lesser width dimension at the interior end of the notch length and tapered along a depth dimension extending between said frame section upper and lower surfaces to diminish along said entire depth dimension from a greater width dimension at said upper frame surface to a lesser width dimension at said lower frame surface.

19. The retractor frame system of claim 18 wherein said notch contours are tapered to accept and frictionally hold hollow elastic tubing having an outside diameter of from about 0.08 inches to about 0.13 inches.

20. The retractor frame system of claim 1 wherein a first plurality of said frame sections are arcuate planar frame sections curved through arcs of ninety degrees and a second plurality of said frame sections are straight planar frame sections.

21. The retractor frame system of claim 20 wherein said plurality of frame sections includes four of said arcuate planar frame sections and at least two of said straight planar frame sections.

* * * * *